(12) United States Patent
Yao et al.

(10) Patent No.: US 6,432,052 B1
(45) Date of Patent: Aug. 13, 2002

(54) HEALTH EXAMINATION CARD FOR FAMILY USE AND IT'S INTERPRETER

(76) Inventors: Chongde Yao; Weimin Peng; Zhong Li, all of 1710 Grandtech Centre, 8 On Ping Street, Shatin (HK)

( * ) Notice: Subject to any disclaimer, the term of this patent is extended or adjusted under 35 U.S.C. 154(b) by 0 days.

(21) Appl. No.: 09/538,044

(22) Filed: Mar. 29, 2000

(30) Foreign Application Priority Data

Jul. 30, 1999 (CH) .......................... 99236748.4

(51) Int. Cl.[7] .............. A61B 5/00; G01J 3/46; G05N 21/25
(52) U.S. Cl. .......... 600/367; 600/362; 600/309; 356/402; 356/400
(58) Field of Search ................. 600/367, 309, 600/362, 365, 360, 345, 551; 204/403; 422/56

(56) References Cited

U.S. PATENT DOCUMENTS

| | | | | |
|---|---|---|---|---|
| 4,871,258 A | * | 10/1989 | Herpichboehm et al | 356/422 |
| 4,989,983 A | * | 2/1991 | Terada et al | 356/423 |
| 5,011,290 A | * | 4/1991 | Terada et al | 356/423 |
| 5,160,979 A | * | 11/1992 | Ota et al | 356/423 |
| 5,266,179 A | * | 11/1993 | Nankai et al | 204/403 |
| 5,279,294 A | * | 1/1994 | Anderson et al | 600/322 |
| 5,304,468 A | * | 4/1994 | Phillips | 435/14 |
| 5,443,080 A | * | 8/1995 | D'Angelo et al | 600/573 |
| 5,507,288 A | * | 4/1996 | Bocker et al | 600/322 |
| 5,695,623 A | * | 12/1997 | Michel et al | 204/403 |
| 5,728,352 A | * | 3/1998 | Poto et al | 422/56 |
| 5,872,713 A | * | 2/1999 | Doublas et al | 204/403 |

* cited by examiner

*Primary Examiner*—Kevin Shaver
*Assistant Examiner*—Navin Natnithithadha
(74) *Attorney, Agent, or Firm*—Jenkens & Gilchrist, P.C.

(57) ABSTRACT

A health examination card and its explainer wherein the health examination card can be used to test the biochemical items of blood (BLD), bilirubin (BIL), urobilinogen (URO), protein (PRO), nitrite (NIT), glucose (GLU), free calcium (Ca), etc and the card explainer can be used to analyze the test results of the above items so as to inspect the health status and provide the early indication of the diseases for finding diseases early. Besides, said examination card and its explainer is easy to use.

9 Claims, 3 Drawing Sheets

HEALTH EXAMINATION CARD FOR FAMILY USE AND IT'S INTERPRETER

The present invention relates to an appliance for health examination, especially a health examination card and its explainer that can be used at home for self-health care.

For long, it is well known that using urine diagnosis test papers in many biochemical tests of human body can provide important references for disease diagnoses. However, these tests are all carried out in the hospital, besides, these tests are very bothering. Hence, most people are afraid of the bother and do not go to the hospital. This is very unfavorable for the early-find of diseases. Thus, it is advantageous for the whole-people health care to simplify and popularize the test method on the basis of the feature that urine diagnosis test papers reflect the test results through color changes.

The object of the present invention is to provide a health examination card and its explainer that facilitate self inspecting health status. This health examination card and its explainer can be conveniently used to inspect the health condition of family members at home and other places so as to find symptoms of diseases early and annihilate the disease at its early stage.

The health examination card of the present invention comprises a test strip (i.e. carrier) that is made of a transparent or white plastic sheet being 2.0–10.0 mm wide, 40.0–150.0 mm long or 21.0–56.0 mm wide, 40.0–100.0 mm long. The blood (BLD), bilirubin (BIL), urobilinogen (URO), protein (PRO), nitrite (NIT), glucose (GLU), free calcium (Ca), etc. test paper patches having semi-quantitative test function and capable of biochemical test are attached on the test strip in a particular sequence and at fixed intervals. A recognizable hand-hold label is marked on the test strip. The test strip is shaped as a rectangular strip. The test paper patches attached on the strip are square. The card explainer of the present invention consists of a LCD screen, a specially designed core element and input keys made from plastic or rubber. The input keys are laterally arranged in 7 rows from top to bottom corresponding to the sequence of test paper patches on the test strip and these rows respectively represent the biochemical test items of blood (BLD), bilirubin (BIL), urobilinogen (URO), protein (PRO), nitrite (NIT), glucose (GLU), free calcium (Ca), etc. On the surfaces of the input keys, there are printed the different reference colors corresponding to the gradient of the semi-quantitative density reaction color of each test paper patch. These keys are longitudinally divided into five groups that respectively represent the test results of (–), +, ++, +++, ++++. The analysis program of each above biochemical test item is incorporated in the core element. The core element is connected to each key through electronic circuits. The health examination card is hermetically packaged in single or 2–5 strips with drying agent. Each package of the health examination card is allotted with a card explainer.

The health examination card and its explainer of the present invention will now be described by way of example with reference to the accompanying drawings.

Figure 1:
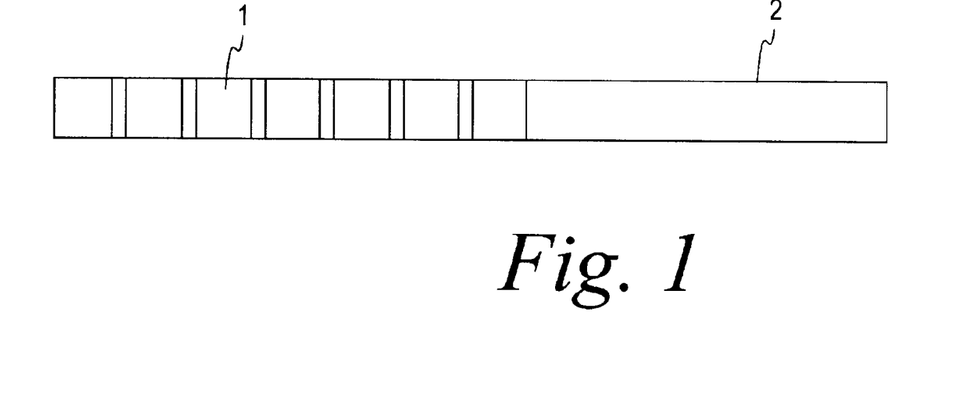
FIG. 1 is a schematic view illustrating the structure of a health examination card of an embodiment according to the present invention.
Figure 2:
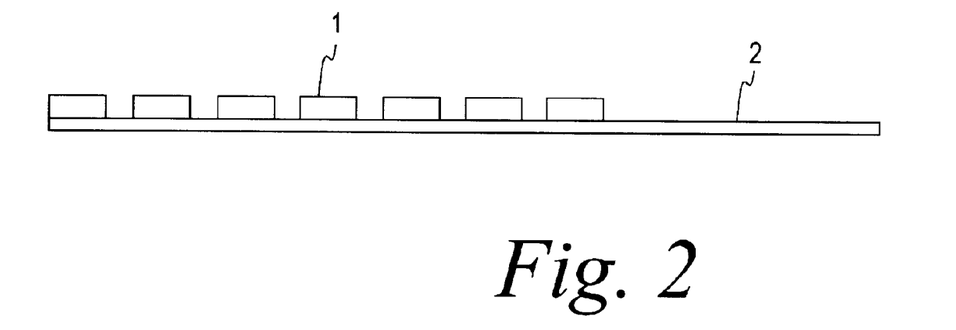
FIG. 2 is a side schematic view of a health examination card of an embodiment according to the present invention.
Figure 4:
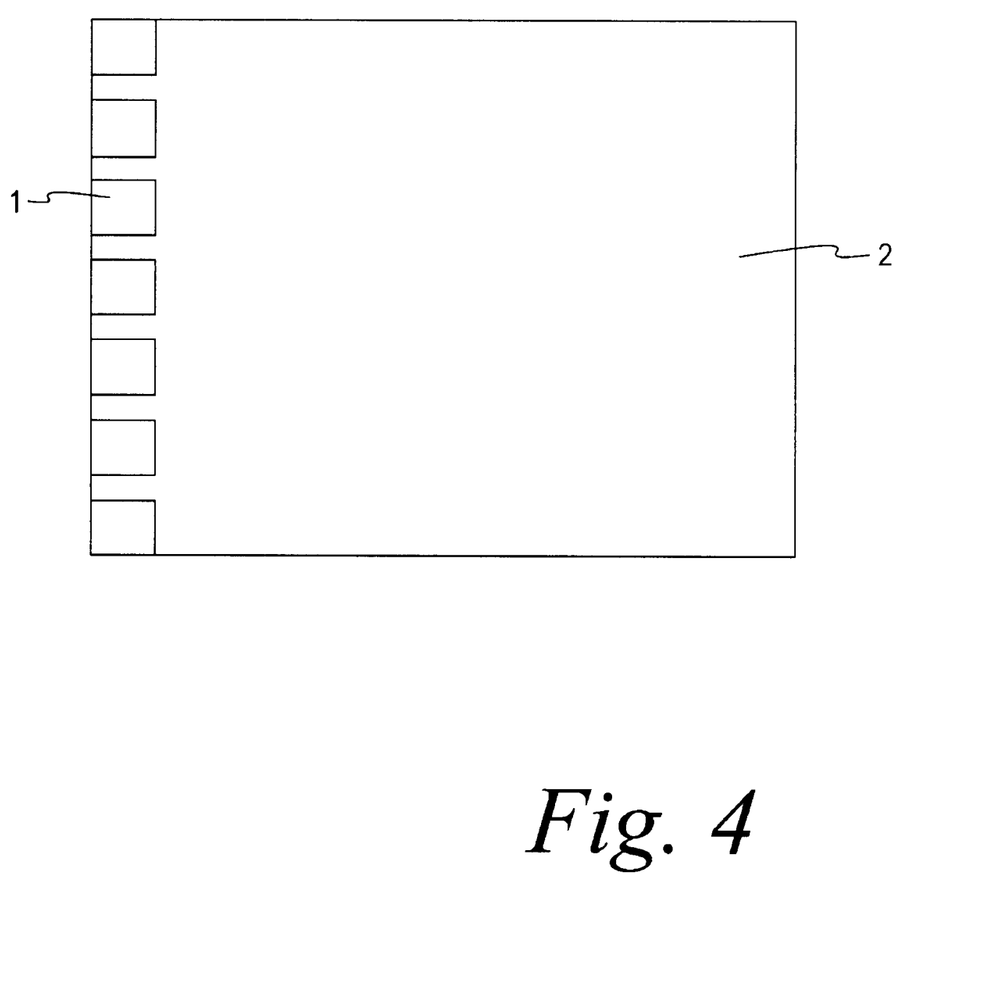
FIG. 4 is a schematic view illustrating the structure of a health examination card of another embodiment according to the present invention.

With reference to FIGS. 1, 2 and 4, the health examination card of the present invention consists of a test strip 2 and test paper patches 1. The test strip 2 is shaped as a rectangular strip. It is 2.0–10.0 mm wide, 40.0– 150.0 mm long or 21.0–56.0 mm wide, 40.0–100.00 mm long. A plurality of small square test paper patches I are attached on the upper surface of the test strip 2. The different pathology index reactants are pasted on the test paper patches.

Figure 3:
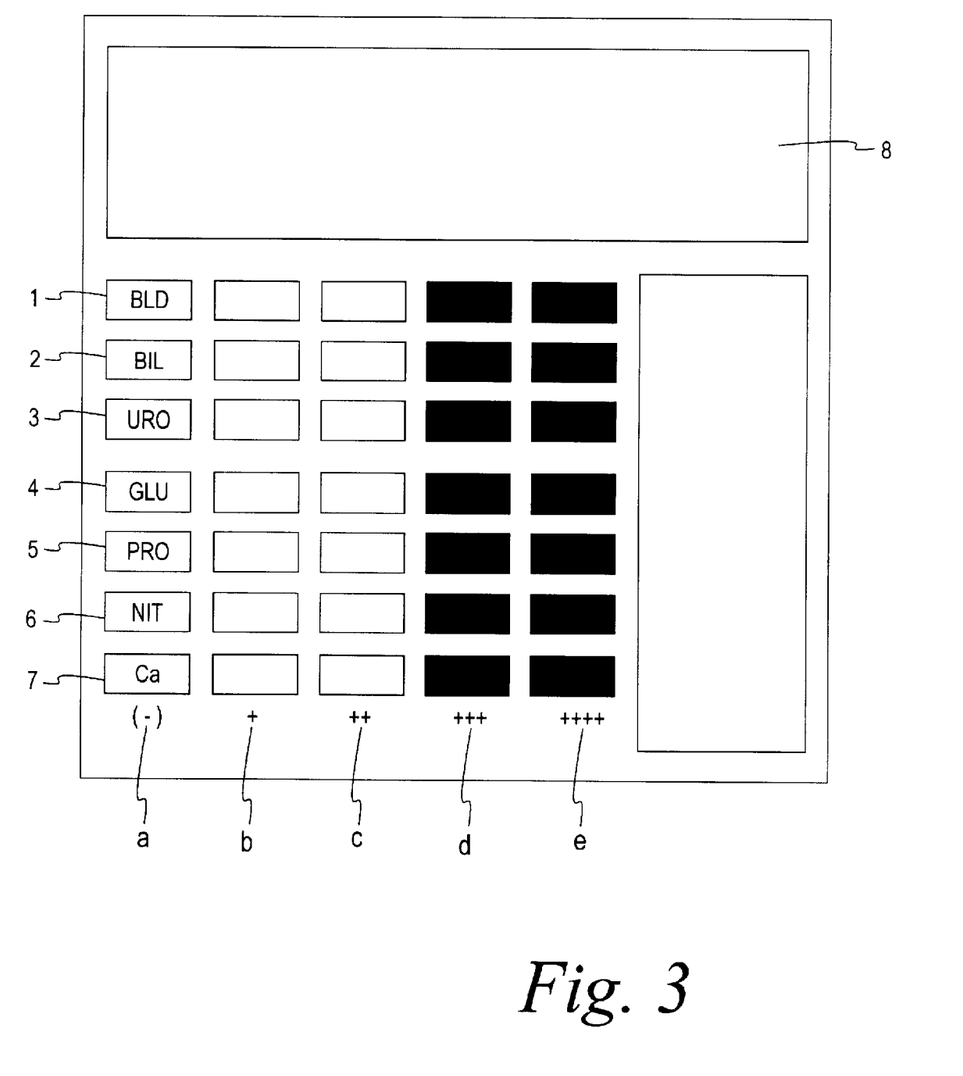
FIG. 3 is a schematic view illustrating the structure of a card explainer of an embodiment according to the present invention.

With reference to FIG. 3, the card explainer of the present invention consists of input keys 1, 2, 3, 4, 5, 6, 7 and LCD screen 8. Five groups of reference colors a, b, c, d, e corresponding to the gradient of semi-quantitative density reaction color of each test paper patch attached on the test strip are printed on the surfaces of the input keys and respectively represent the test results of (–), +, ++, +++, ++++.

Upon use, the user takes out the health examination card from the package and holds the portion of the test strip on which a remarkable hand-hold label is marked, and then dips the test paper patches attached on the test strip into the urine entirely and takes out in 2 seconds. Afterwards, the reaction color of each diagnosis test paper is compared with the reference color of the same item on the card explainer. The input key with the same color as the test paper is found out and pressed. Then the LCD screen displays the test result of this item as well as the matters needing attention. Because the present invention integrates the usual diagnosis items and uses the colored keys to represent a variety of test results of the test paper, it makes people feel simple and convenient, moreover, the objects that inspecting health at home so as to find diseases early can be accomplished.

What is claimed:

1. A method for providing a test report for a plurality of biochemical test items of a health examination card comprising dipping the health examination card with a plurality of test paper patches attached thereon which correspond to the biochemical test items into the human body fluid to be tested, then taking the card out of the body fluid after a predetermined time, and then inputting a semi-quantitative density reaction color of each test paper patch into an interpreter for said health examination card, said interpreter providing a test report including a test result as well as an identification of the matters needing attention.

2. A method as set forth in claim 1, wherein said test items may be selected from blood (BLD), bilirubin (BIL), urobilinogen (URO), protein (PRO), nitrite (NIT), glucose (GLU), free calcium (Ca).

3. A method as set forth in claim 1, wherein said method may be used to analyze urine, blood (serum), saliva.

4. A health examination card comprising a test strip and test paper patches having semi-quantitative density test function and capable of biochemical testing, said test paper patches are attached on the test strip in a particular sequence and at fixed intervals, and, said test paper patches correspond to the biochemical test items to be tested.

5. A health examination card as set forth in claim 4, wherein said test strip is 2.0–10.0 mm wide and 40.0–150.0 mm long.

6. A health examination card as set forth in claim 4, wherein said test strip is 21.0–56.0 mm wide and 40.0–100.0 mm long.

7. A health examination card as set forth in claim 4, wherein the sequence of said biochemical items is arbitrary.

8. A health examination card as set forth in claim 4 can be used to analyze urine, blood (serum), saliva etc., wherein a recognizable label is marked on said test strip for directing placement of a use's hand.

9. A health examination card, comprising a housing, input keys, a LCD screen and a core element, said input keys are arranged corresponding to types of test paper patches attached on the health examination card, for said types of test paper patches five input keys are assigned, colors of a surface of the input keys respectfully correspond to semi-quantitative density reaction colors of a respective test paper patch from a light color to a dark color, which respectively represent a test result of (−), +, ++, +++, ++++, an analysis program is stored in the core element, when an input key is pressed, the analysis program stored in the core element will output a report including the test result as well as information from the analysis program requiring attention onto the LCD screen for the biochemical item represented by said input key.

* * * * *

UNITED STATES PATENT AND TRADEMARK OFFICE
CERTIFICATE OF CORRECTION

PATENT NO. : 6,432,052 B1
DATED : August 13, 2002
INVENTOR(S) : Chongde Yao et al.

It is certified that error appears in the above-identified patent and that said Letters Patent is hereby corrected as shown below:

<u>Title page,</u>
Item [57], ABSTRACT,

Replace "A health examination card and its explainer wherein the health examination card can be used to test the biochemical items of blood (BLD), bilirubin (BIL), urobilinogen (URO), protein (PRO), nitrite (NIT), glucose (GLU), free calcium (Ca), etc and the card explainer can be used to analyze the test results of the above items so as to inspect the health status and provide the early indication of the diseases for finding diseases early. Besides, said examination card and its explainer is easy to use."

With --A health examination card and its interpreter wherein the health examination card can be used to test the biochemical items of blood (BLD), bilirubin (BIL), urobilinogen (URO), protein (PRO), nitrite (NIT)m glucos (GLU), free calcium (Ca), etc. and the card interpreter can be used to analyze the test results of the above items so as to inspect the health status and provide the early indication of the diseases for finding diseases early. Besides, said examination card and its interpreter is easy to use. --

<u>Column 1,</u>
Line 4, insert -- FIELD OF THE INVENTION --
Line 6, replace "explainer" with -- interpreter --

UNITED STATES PATENT AND TRADEMARK OFFICE
CERTIFICATE OF CORRECTION

PATENT NO. : 6,432,052 B1
DATED : August 13, 2002
INVENTOR(S) : Chongde Yao et al.

It is certified that error appears in the above-identified patent and that said Letters Patent is hereby corrected as shown below:

<u>Column 1, cont'd,</u>
Lines 7-16,

Replace "For long, it is well known that using urine diagnosis test papers in many biochemical tests of human body can provide important references for disease diagnoses. However, these tests are all carried out in the hospital, besides, these tests are very bothering. Hence, most people are afraid of the bother and do not go to the hospital. This is very unfavorable for the early-find of diseases. Thus, it is advantageous for the whole-people health care to simplify and popularize the test method on the basis of the feature that urine diagnosis test papers reflect the test results through color changes."

With --It is well known that using urine-diagnosis test papers in many biochemical tests of the human body can provide important references for disease diagnoses. However, these tests are all carried out in the hospital. In addition, these test are very bothersome. Hence, most people are afraid or troubled by the tedium and do not go to the hospital. This is very unfavorable for the earl-detection of diseases. Thus, it is advantageous for the health care of all people to simplify and popularize the test method on the basis of the feature that urine diagnosis test papers reflect the test results through color changes.--

UNITED STATES PATENT AND TRADEMARK OFFICE
CERTIFICATE OF CORRECTION

PATENT NO. : 6,432,052 B1
DATED : August 13, 2002
INVENTOR(S) : Chongde Yao et al.

It is certified that error appears in the above-identified patent and that said Letters Patent is hereby corrected as shown below:

<u>Column 1, cont'd,</u>
Line 17, insert -- SUMMARY OF THE INVENTION --
Line 18, replace "its explainer that" with -- its interpreter to --
Line 20, replace "explainer" with -- interpreter --
Lines 24-53, > Replace "The health examination card of the present invention comprises a test strip (i.e. carrier) that is made of a transparent or white plastic sheet being 2.0-10.0 mm wide, 40.0-150.0 mm long or 21.0-56.0 mm wide, 40.0-100.0 mm long. The blood (BLD), bilirubin (BIL), urobilinogen (URO), protein (PRO), nitrite (NIT), glucose (GLU), free calcium (Ca), etc. test paper patches
>
> having semi-quantitative test function and capable of biochemical test are attached on the test strip in a particular sequence and at fixed intervals. A recognizable hand-hold label is marked on the test strip. The test strip is shaped as a rectangular strip. The test paper patches attached on the strip are square. The card explainer of the present invention consists of a LCD screen, a specially designed core element and input keys made from plastic or rubber. The input keys are laterally arranged in 7 rows from top to bottom corresponding to the sequence of test paper patches on the test strip and these rows respectively represent the biochemical test items of blood (BLD), bilirubin (BIL), urobilinogen (URO), protein (PRO), nitrite (NIT), glucose (GLU), free calcium (Ca), etc. On the surfaces of the input keys, there are printed the different

UNITED STATES PATENT AND TRADEMARK OFFICE
CERTIFICATE OF CORRECTION

PATENT NO.     : 6,432,052 B1
DATED          : August 13, 2002
INVENTOR(S)    : Chongde Yao et al.

It is certified that error appears in the above-identified patent and that said Letters Patent is hereby corrected as shown below:

<u>Column 1, cont'd,</u> reference colors corresponding to the gradient of the semi-quantitative density reaction color of each test paper patch. These keys are longitudinally divided into five groups that respectively represent the test results of (-), +, ++, +++, ++++. The analysis program of each above biochemical test item is incorporated in the core element. The core element is connected to each key through electronic circuits. The health examination card is hermetically packaged in simgle or 2-5 strips with drying agent. Each package of the health examination card is allotted with a card explainer."

With --The health examination card of the present invention comprises a test strip (i.e. carrier) that is made of a transparent or white plastic sheet being 2.0-10.0mm wide, 40.0-150.0mm long or 21.0-56.0mm wide, 40.0-100.0mm long.

The blood (BLD), bilirubin (BIL), urobilinogen (URO), protein (PRO), nitrite (NIT), glucose (GLU), free calcium (Ca), etc. test paper patches having semi-quantitative test functions and capable of biochemical testing are attached on the test strip in a particular sequence and at fixed intervals. A recognizable label for placement of the hand where the strip is to be held is marked on the test strip. The test strip is shaped as a rectangular strip. The test paper patches attached on the strip are of square shape. The card interpreter of the present invention consists of a LCD screen, a specially designed core element and input keys made from plastic or rubber. The input keys are arranged in 7 rows from top to bottom corresponding to the sequence of test paper patches on the test strip. These rows respectively represent the biochemical test items of blood

UNITED STATES PATENT AND TRADEMARK OFFICE
CERTIFICATE OF CORRECTION

PATENT NO. : 6,432,052 B1
DATED : August 13, 2002
INVENTOR(S) : Chongde Yao et al.

It is certified that error appears in the above-identified patent and that said Letters Patent is hereby corrected as shown below:

Column 1, cont'd,

```
          (BLD), bilirubin (BIL),
          urobilinogen (URO), protein (PRO),
          nitrite (NIT), glucose (GLU), free
          calcium (Ca), etc. On the
          surfaces of the input keys,
          different reference colors are
          printed corresponding to the
          gradient of the semi-quantitative
          density reaction color of each
          test paper patch. These keys are
          divided into five groups that
          respectively represent the test
          results of (-), +, ++, +++, ++++.
          The analysis program of each
          mentioned biochemical test item is
          incorporated in the core element.
          The core element is connected to
          each key through electronic
          circuits. The health examination
          card is hermetically packaged
          along with a drying agent in units
          of one or two to five strips.
          Each package for the health
          examination card is allotted with
          a card interpreter.--
```

Line 54, insert -- "BRIEF DESCRIPTION OF THE DRAWINGS" --
Line 54, replace "its explainer" with -- its interpreter --
Line 63, replace "card explainer" with -- card interpreter --

Column 2,
Lines 1-31,
```
          Replace "With reference to FIGS.
          1, 2 and 4, the health examination
          card of the present invention
          consists of a test strip 2 and
          test paper patches 1. The test
          strip 2 is shaped as a rectangular
          strip. It is 2.0-10.0 mm wide,
          40.0-150.0mm long or 21.0-56.0mm
          wide, 40.0-100.0 mm long. A
          plurality of small square test
          paper patches I are attached on
          the upper surface of the test trip
          2. The different pathology index
          reactants are pasted on the test
          paper patches.
```

UNITED STATES PATENT AND TRADEMARK OFFICE
CERTIFICATE OF CORRECTION

PATENT NO. : 6,432,052 B1
DATED : August 13, 2002
INVENTOR(S) : Chongde Yao et al.

It is certified that error appears in the above-identified patent and that said Letters Patent is hereby corrected as shown below:

Column 2, cont'd,

With reference to FIG. 3, the card explainer of the present invention consists of input keys 1, 2, 3, 4, 5, 6, 7 and LCD screen 8. Five groups of reference colors a, b, c, d, e corresponding to the gradient of semi-quantitative density reaction color of each test paper patch attached on the test strip are printed on the surfaces of the input keys and respectively represent the test results of (-), +, ++. +++,++++.

Upon use, the user takes out the health examination card from the package and holds the portion of the test strip on which a remarkable hand-hold label is marked, and then dips the test paper patches attached on the test strip into the urine entirely and takes out in 2 seconds. Afterwards, the reaction color of each diagnosis test paper is compared with the reference color of the same item on the card explainer. The input key with the same color as the test paper is found out and pressed. Then the LCD screen displays the test result of this item as well as the matters needing attention. Because the present invention integrates the usual diagnosis items and uses the colored keys to represent a variety of test results of the test paper, it makes people feel simple and convenient, moreover, the objects that inspecting health at home so as to find diseases early can be accomplished."

UNITED STATES PATENT AND TRADEMARK OFFICE
CERTIFICATE OF CORRECTION

PATENT NO. : 6,432,052 B1
DATED : August 13, 2002
INVENTOR(S) : Chongde Yao et al.

It is certified that error appears in the above-identified patent and that said Letters Patent is hereby corrected as shown below:

Column 2 cont'd,

With --With reference to Figs. 1, 2 and 4, the health examination card of the present invention consists of a test strip 2 and test paper patches 1. The test strip 2 is shaped as a rectangular strip. It is 2.0-10.0mm wide, 40.0-150.0mm long or 21.0-56.0mm wide, 40.0-100.0mm long. A plurality of small square test paper patches 1 are attached on the upper surface of the test strip 2. Reactants for different pathology indices are pasted on the test paper patches.

With reference to Fig. 3, the card interpreter of the present invention consists of input keys 1, 2, 3, 4, 5, 6, 7, and LCD screen 8. Five groups of reference colors a, b, c, d, e corresponding to the gradient of semi-quantitative density reaction color of each test paper patch attached on the test strip are printed on the surfaces of the input keys and respectively represent the test results of (-), +, ++, +++, ++++.

Upon use, the user takes out the health examination card from the package and holds the portion of the test stip on which a label for placement of the hand is marked, and then dips the test paper

UNITED STATES PATENT AND TRADEMARK OFFICE
CERTIFICATE OF CORRECTION

PATENT NO.    : 6,432,052 B1
DATED         : August 13, 2002
INVENTOR(S)   : Chongde Yao et al.

It is certified that error appears in the above-identified patent and that said Letters Patent is hereby corrected as shown below:

<u>Column 2, cont'd,</u>

```
patches attached on the test strip
completely into the urine and
removes after 2 seconds.
Afterwards, the reaction color of
each diagnosis test paper is
compared with the reference color
of the same item on the card
interpreter.  The input key with
the same color as the test paper
is determined and pressed.  Then
the LCD screen displays the test
result of this item as well as the
matters needing attention.
Because the present invention
integrates the usual diagnosis
items and uses the colored keys to
represent a variety of test
results of the test paper, it
pleases people due to its
simplicity and convenience.
Moreover, the objects of
monitoring health at home so as to
find diseases early can be
accomplished.--
```

Signed and Sealed this

Seventh Day of October, 2003

JAMES E. ROGAN
*Director of the United States Patent and Trademark Office*